(12) United States Patent
    Gregory

(10) Patent No.: US 11,951,279 B2
(45) Date of Patent: Apr. 9, 2024

(54) CARTRIDGE INSERTION MECHANISM FOR A FLUID DELIVERY DEVICE

(71) Applicant: MannKind Corporation, Danbury, CT (US)

(72) Inventor: Christopher C. Gregory, Newtown, PA (US)

(73) Assignee: MannKind Corporation, Danbury, CT (US)

( * ) Notice: Subject to any disclaimer, the term of this patent is extended or adjusted under 35 U.S.C. 154(b) by 282 days.

(21) Appl. No.: 16/388,342

(22) Filed: Apr. 18, 2019

(65) Prior Publication Data

US 2019/0240399 A1    Aug. 8, 2019

Related U.S. Application Data

(63) Continuation of application No. 15/512,907, filed as application No. PCT/US2015/055117 on Oct. 12, 2015, now Pat. No. 10,307,529.

(60) Provisional application No. 62/063,979, filed on Oct. 15, 2014.

(51) Int. Cl.
    *A61M 5/142* (2006.01)
    *A61M 5/145* (2006.01)
    *A61M 5/28* (2006.01)

(52) U.S. Cl.
    CPC .... *A61M 5/14248* (2013.01); *A61M 5/14526* (2013.01); *A61M 5/288* (2013.01); *A61M 2005/14513* (2013.01); *A61M 2005/14573* (2013.01)

(58) Field of Classification Search
    CPC .......... A61M 5/14248; A61M 5/14526; A61M 5/288; A61M 2005/14513; A61M 2005/14573

USPC ......................................................... 604/152
    See application file for complete search history.

(56) References Cited

U.S. PATENT DOCUMENTS

| | | | |
|---|---|---|---|
| 3,767,085 A * | 10/1973 | Cannon | B05C 17/00566 604/82 |
| 6,406,455 B1 * | 6/2002 | Willis | A61M 5/30 604/82 |
| 2004/0111063 A1 | 6/2004 | Botitch et al. | |
| 2009/0227958 A1 | 9/2009 | Burroughs et al. | |

(Continued)

FOREIGN PATENT DOCUMENTS

| | | |
|---|---|---|
| JP | 2013-528113 A | 8/2013 |
| WO | 2006031500 A2 | 3/2006 |

OTHER PUBLICATIONS

First Office Action dated Mar. 6, 2019 for Chinese Patent Application No. 201580054065.7, 7 pages.

(Continued)

*Primary Examiner* — Phillip A Gray
(74) *Attorney, Agent, or Firm* — Morgan, Lewis & Bockius LLP

(57) ABSTRACT

A fluid delivery device comprises a drive unit including an actuator and one or more first features and a cartridge filled with a fluid prior to being inserted into the housing. The cartridge having a fluid reservoir sealed at one end by a movable piston and sealed at another end by a pierceable septum. The cartridge includes one or more second features that are configured to align and mate with the one or more first features allowing the cartridge to be inserted into the drive unit. The piston is moveable by the actuator once the cartridge is inserted into the drive unit.

29 Claims, 8 Drawing Sheets

(56) References Cited

U.S. PATENT DOCUMENTS

| | | |
|---|---|---|
| 2009/0240232 A1 | 9/2009 | Gonnelli et al. |
| 2011/0282300 A1 | 11/2011 | Kriesel et al. |
| 2011/0306929 A1* | 12/2011 | Levesque .......... A61M 5/14248 |
| | | 604/150 |
| 2012/0203185 A1 | 8/2012 | Kristensen et al. |
| 2013/0090602 A1 | 4/2013 | Avery et al. |
| 2013/0096509 A1* | 4/2013 | Avery ................. A61M 5/3129 |
| | | 604/189 |
| 2013/0150786 A1 | 6/2013 | Hiles |
| 2014/0163468 A1 | 6/2014 | Avery et al. |

OTHER PUBLICATIONS

Extended European Search Report for corresponding European Patent Application No. 20171734.5, dated Aug. 13, 2020, 10 pages.
Office Action dated Apr. 2, 2018 for Japanese Patent Application No. 2017-516417, 4 pages.
Extended European Search Report dated Feb. 16, 2018 for European Patent Application No. 15850644.4, 5 pages.
Supplementary European Search Report dated Mar. 12, 2018 for European Patent Application No. 15850644.4, 3 pages.
International Search Report dated Jan. 5, 2016 for International Application No. PCT/US2015/055117, pp. 3.
Written Opinion dated Jan. 5, 2016 for International Application No. PCT/US2015/055117, pp. 6.

* cited by examiner

CARTRIDGE INSERTION MECHANISM FOR A FLUID DELIVERY DEVICE

CROSS-REFERENCE TO RELATED APPLICATIONS

This application is a continuation of U.S. patent application Ser. No. 15/512,907 filed on Mar. 21, 2017, which is a U.S. National Stage filing of International Patent Application No. PCT/US15/55117 filed Oct. 12, 2015, which claims the benefit of U.S. Provisional Patent Application No. 62/063,979 filed Oct. 15, 2014 entitled "Cartridge Insertion Mechanism for a Fluid Delivery Device", each of which are incorporated by reference herein in their entirety.

BACKGROUND OF THE INVENTION

The present invention generally relates to cartridge insertion mechanisms for fluid delivery devices and, more particularly, to cartridge insertion mechanisms for ambulatory fluid delivery pumps for delivering a medicament to a patient.

BRIEF DESCRIPTION OF THE SEVERAL VIEWS OF THE DRAWINGS

The following detailed description of embodiments of the cartridge insertion mechanisms for a fluid delivery device, will be better understood when read in conjunction with the appended drawings of exemplary embodiments. It should be understood, however, that the invention is not limited to the precise arrangements and instrumentalities shown.

In the drawings.

DETAILED DESCRIPTION OF THE INVENTION

Referring to FIGS. 1-3B, an exemplary fluid delivery device 110 is shown. In one embodiment, fluid delivery device 110 is a discrete ambulatory insulin delivery pump. Fluid delivery device 110 may be single use, disposable and incapable of reuse. Fluid delivery device 110 may provide therapeutic capability in a small, single use, disposable package and can be produced using high volume manufacturing fabrication (e.g., injection molding) and assembly processes, allowing for low cost of goods. Devices of the invention can be used for a broad range of applications, including, but not limited to, clinical applications (e.g., administration of medicaments, etc.) and biomedical research (e.g., microinjection into cells, nuclear or organelle transplantation, isolation of single cells or hybridomas, etc.).

In one embodiment, fluid delivery device 110 is a device for dispensing, delivering, or administering the fluid or agent to the user or patient. The fluid may be a low viscosity gel agent and or a therapeutic agent. In one embodiment, the fluid is an analgesic agent. In one embodiment, the fluid is insulin of any type. In one embodiment, the fluid is a U100 insulin. In another embodiment the fluid is a U200 insulin. In another embodiment, the fluid is a U300 insulin. In another embodiment, the fluid is a U500 insulin. In another embodiment, the fluid is any insulin between U100 and U500. In other embodiments, the fluid may be, but is not limited to, opiates and/or other palliatives or analgesics, hormones, psychotropic therapeutic compositions, or any other drug or chemical whose continuous dosing is desirable or efficacious for use in treating patients. Single fluids and combinations of two or more fluids (admixed or co-administered) may be delivered using fluid delivery device 110. As used herein "patients" or "user" can be human or non-human animals; the use of fluid delivery device 110 is not confined solely to human medicine, but can be equally applied to veterinarian medicine.

Fluid delivery device 110 may dispense the fluid over a sustained period of time (i.e., basal delivery). In one embodiment, the fluid delivery rate is continuously or near continuously delivered to the user over the sustained period of time. Fluid delivery device 110 may also be capable of dispensing a supplementary amount of fluid, in addition to the basal amount, on demand, under patient control (i.e., bolus delivery). In one embodiment, the bolus amount delivered in a single, selectable administration is pre-determined. In preferred embodiments, fluid delivery device 110 is hydraulically actuated and comprises one or more reservoirs or chambers containing hydraulic fluid of a suitable viscosity for transferring power from one or more actuators to the fluid and controlling the delivery rate as discussed further below.

Figure 1:
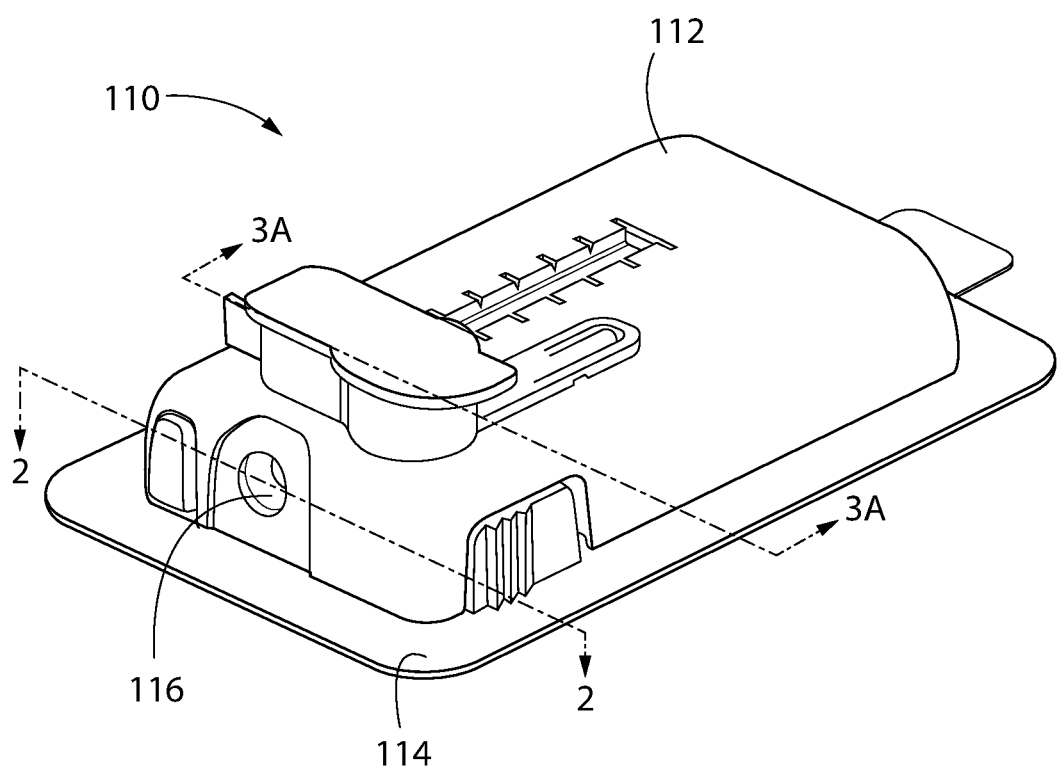
FIG. 1 is a trimetric view of a fluid delivery device.

Referring to FIG. 1, for example, the fluid delivery device 110 shown includes a housing 112 and an adhesive bottom surface 114 such as a foam pad.

Figure 2:
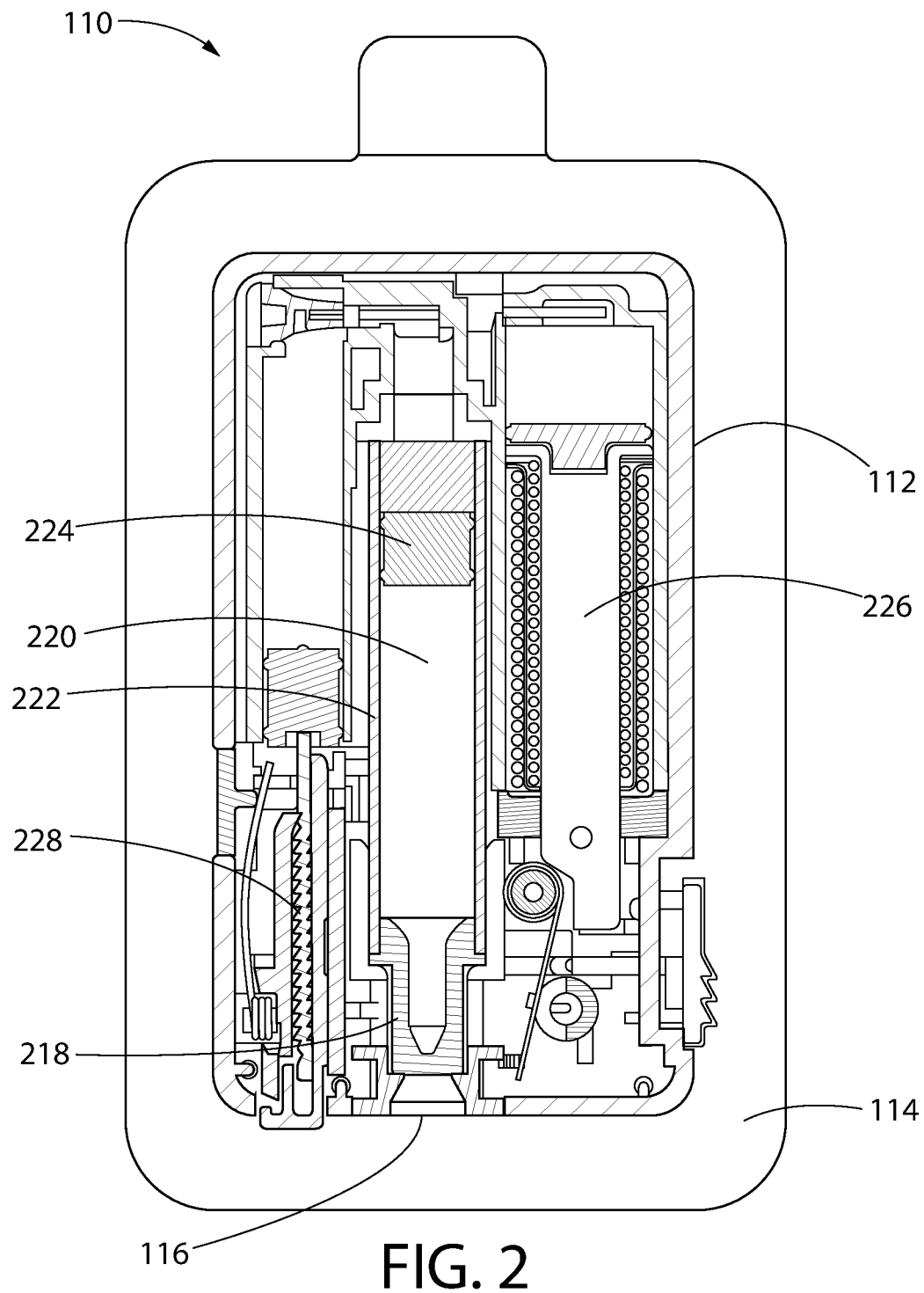
FIG. 2 is a top cross sectional view of the fluid delivery device shown in FIG. 1 taken along a plane indicated by line 2-2.

Referring to FIG. 2, fluid delivery device 110 includes a cartridge 222 having a fluid reservoir 220 containing the medicament. The fluid delivery device 110 may include one or more actuators 226 (such as a basal actuator), 228 (such as a bolus actuator) that act on piston 224 within cartridge 222.

Figure 3A:
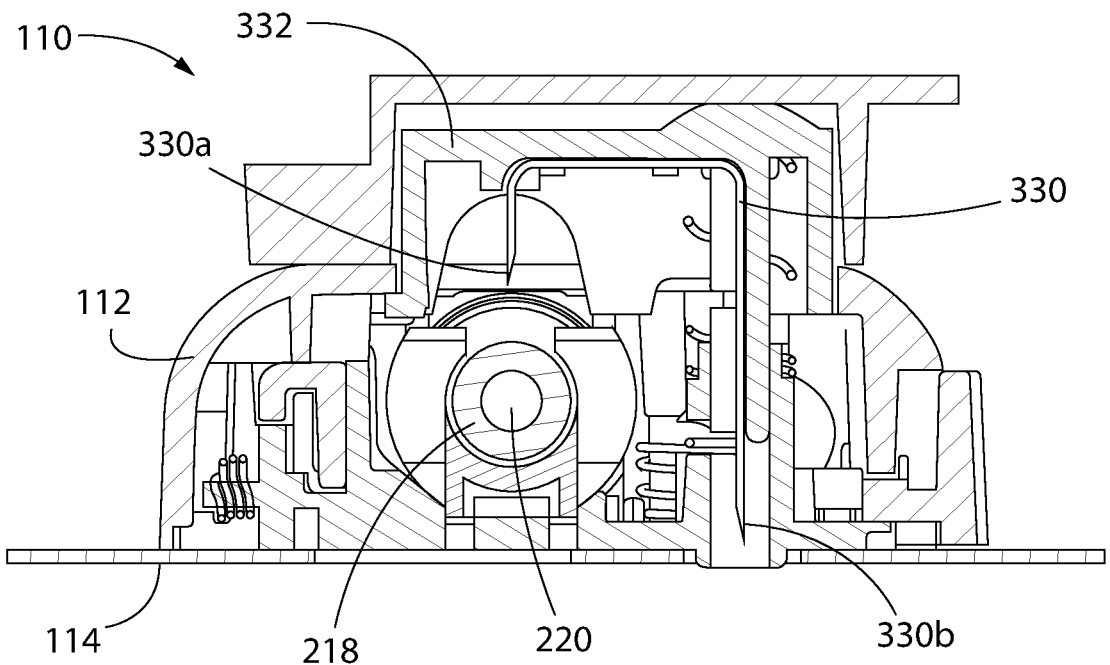
FIG. 3A is a front cross sectional view of the fluid delivery device shown in FIG. 1 taken along a plane indicated by line 3A-3A and shown in the initial position.
Figure 3B:
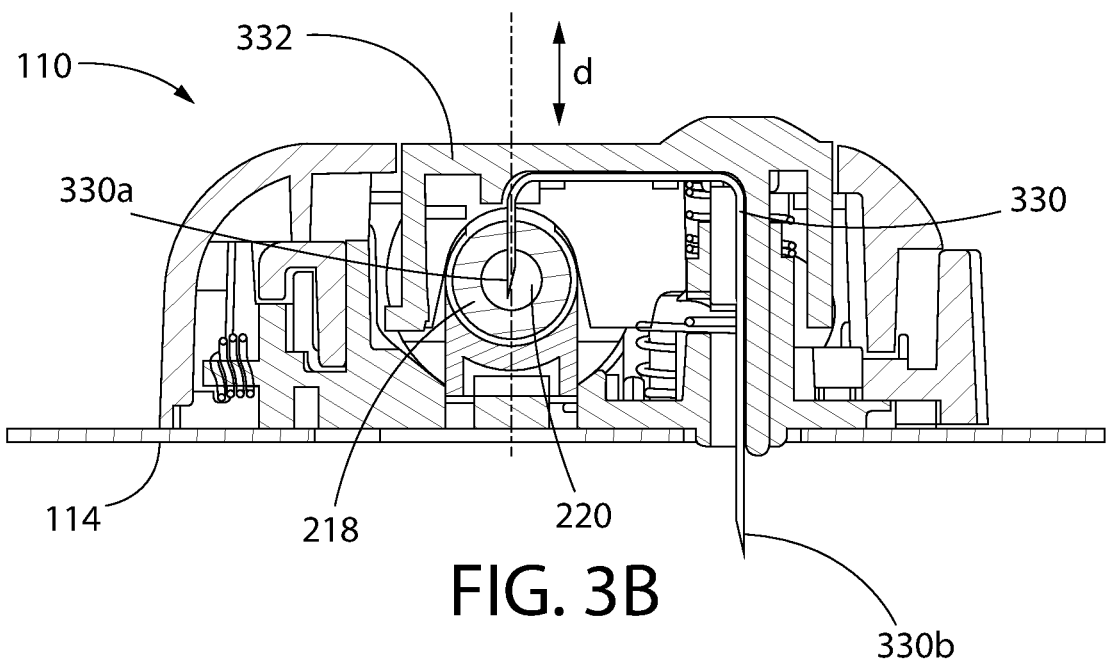
FIG. 3B is a front cross sectional view of the fluid delivery device of FIG. 3A shown in the deployed position.
Figure 4:
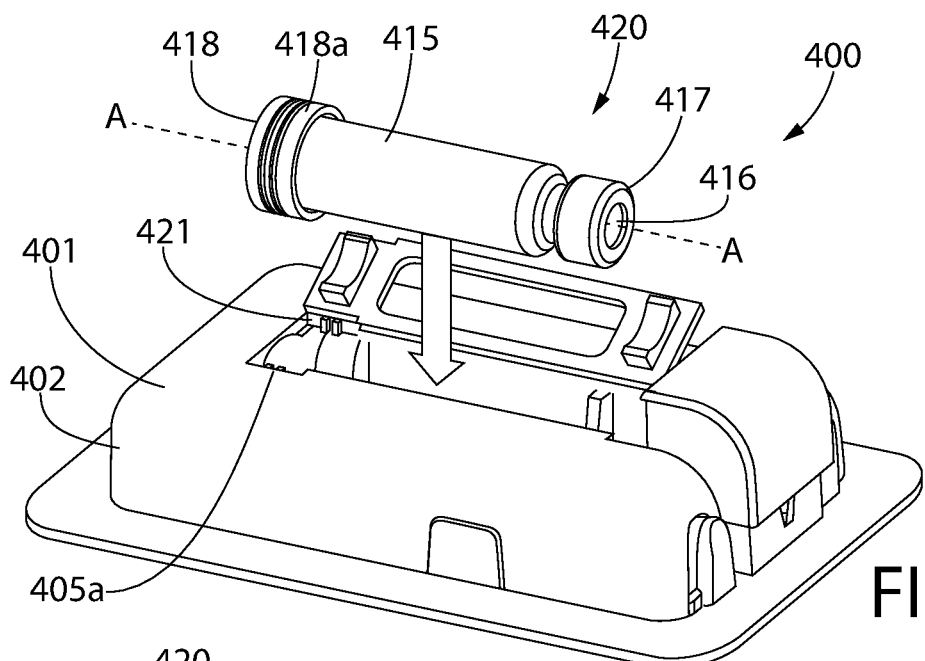
FIG. 4 is a trimetric view of a fluid delivery device with an insertable cartridge in accordance with an exemplary embodiment of the present invention illustrating the cartridge being inserted.

Referring to FIGS. 3A and 3B, a needle 330 may be deployed to fluidly couple fluid reservoir 220 and the patient. Needle 330 may be coupled to a button 332 and the needle 330 may be bent such that a translation of button 332 toward the patient causes a fluid coupling end 330a to be fluidly coupled to fluid reservoir 220 and a delivery end 330b to extend from bottom surface 114.

Liquid pharmaceuticals for subcutaneous delivery mendicants are commonly packaged in cartridge or vials having a fluid reservoir. It is desirable to be able to load these prefilled cartridges into a fluid delivery device for ease of handling rather than have to fill a reservoir already inside of the device.

The cartridges commonly have a septum seal on one end and a piston or plunger inside at an opposite end. The medicament is delivered by fluidly connecting the material inside of the cartridge through the septum with the patient's body and then pressing on the piston.

In most fluid delivery systems, and especially in hydraulically driven fluid delivery devices, the accurate and effective delivery of the medicament requires that there be little, and preferably no, compressible gaps between the drive mechanism and the piston, little, and preferably no, pre-delivery pressure on the piston and that the needle be accurately inserted into the septum.

Inserting a cartridge in a delivery device can result in performance issues due to the length tolerance of the cartridge resulting in unacceptably large gaps that are compressible between the drive mechanism and the piston and a misaligned needle insertion system.

In addition, temperature changes in storage and transport may cause changes in component dimensions and liquid volumes. If there is a significant difference in the coefficients of thermal expansion between components, then there may be significant changes in the components positions which could exacerbate tolerance issues. This is especially significant in hydraulically driven systems where the fluid is likely to have much greater thermal expansion characteristics than the solid components of the device.

It is therefore desired to have a simple to use mechanism that allows a prefilled fluid reservoir or cartridge to be inserted in a delivery device, create a fluid seal to the device minimizing compressible gaps between the drive mechanism and the piston. In one embodiment, the length tolerance of the cartridge usable with the delivery device is at least +/−0.4 mm. The delivery device may allow for minimal pressure in the system due to insertion or the insertion mechanism. The delivery device may allow for proper alignment between the cartridge septum seal and the needle mechanism. It is also beneficial if the delivery device can compensate for thermal expansion effects.

Referring to the drawings in detail, wherein like reference numerals indicate like elements throughout, there is shown in FIGS. 4-12 fluid delivery devices in accordance with exemplary embodiments of the present invention. Embodiments of the cartridge configuration may be used with various fluid delivery devices 110 (see FIGS. 1-3B) such as the fluid delivery devices disclosed in U.S. Pat. Nos. 9,101,706, 8,740,847, and 7,481,792 that are hereby incorporated by reference in their entirety.

In some embodiments, the fluid delivery device 110, 400 includes a housing and a bottom surface configured to be coupled to a skin surface in an engaged position. In one embodiment, a cartridge having a fluid reservoir is coupled to the housing and has a septum. In one embodiment, the septum seals one end of the fluid reservoir and a piston (see FIG. 2) seals the other end. In one embodiment, the patient inserts a pre-filled cartridge into the fluid delivery device prior to use. The septum of the cartridge may have a pierceable portion, the portion of the septum pierced by the needle during use. In one embodiment, the cartridge is comprised of glass, or has an inner glass coating, though other materials for the cartridge such as plastic may be used.

In some embodiments, a needle assembly having a needle may be used to fluidly couple the septum with the skin surface with the desired motion by the user or be configured to automatically deploy upon use of the device. The needle may have a delivery end and a fluid coupling end. Initially, the fluid coupling end may be fluidly disengaged from the fluid reservoir, (e.g., an initial or pre-fluid delivery position). The delivery end of the needle may also be spaced above the bottom surface of the fluid delivery device such that both ends of needle are contained within the housing in the initial position. After the fluid delivery device is adhered to the skin surface in the engaged position, the delivery end of the needle may be extended through the bottom surface of the fluid delivery device and the fluid coupling end of the needle may be extended through the pierceable portion of the septum either simultaneously, at offset times or separately such that fluid reservoir is fluidly coupled with the patient during use (e.g., a deployed, in-use or fluid delivery position).

In some embodiments, where the system is driven by a fluid, the fluid must be contained securely in the device prior to the cartridge being installed. Once installed, the fluid or fluid driven element is operable to urge or push the cartridge piston with minimal and preferably no compressible space between the two.

Referring to FIGS. 4-11, a first exemplary embodiment of a fluid delivery device 400 is shown. The fluid delivery device 400 may comprise two main components, the hydraulic drive unit 401 and the insertable prefilled cartridge 420. In one embodiment, the cartridge 420 includes a fluid reservoir 415, containing a medicament, sealed at one end with a piercable element 416 such as a septum held in place by a crimp cover 417 and sealed at the other end by an internally movable piston 419 (see FIG. 9). The cartridge 420 also may also include a keyed feature 418 at one end. In other embodiments, the keyed feature 418 is proximate the middle and/or other end of the cartridge 420. In one embodiment, the keyed feature 418 is part of a sleeve as shown in FIGS. 4-11, at the piston end of the fluid reservoir 415 that is attached to the outer surface of the cartridge 420 and is configured to mate with the hydraulic drive unit 401 upon insertion of the cartridge 420 into the hydraulic drive unit 401. In one embodiment, the keyed feature 418 has one or more features 418a such as radially protecting indentations and/or protrusions that are unique to the model of the cartridge that mate with one or more corresponding features of the hydraulic drive unit 401. This keyed configuration between the cartridge 420 and the drive unit 401 may help to prevent a cartridge 420 not intended for the specific drive unit 401, such as a cartridge containing an undesirable type or volume of medicament, from being inserted into the specific drive unit 401.

In the embodiment shown in FIGS. 4-11, the features 418a of the cartridge 420 include one or more groves that correspond with features 421 such as protrusions of the drive unit 401. In other embodiments, the features 418a of the cartridge 420 also or alternatively include protrusions that correspond with the features 421 of the drive unit 401 such as indentations. In one embodiment, the one or more features 418*a* of the keyed feature 418 project radially inwardly and/or outwardly relative to a longitudinal axis A of the cartridge 420 and extend around the entire circumference of the keyed feature 418 such that the cartridge 420 may be inserted into the hydraulic drive unit 401 in any radial position about axis A. In other embodiments, the one or more features 418*a*, 421 extend only partially around the circumference of the keyed feature 418 and/or the drive unit such that the cartridge 420 may only be inserted into the drive unit 401 in one or more discrete radial positions about axis A.

In one embodiment, the features 421 of the drive unit 401 are proximate the seal receptacle 408 within the hydraulic drive unit. The drive unit 401 may include an actuator that drives a hydraulic fluid configured to drive the piston 419. The drive unit 401 may be positioned within a housing 402.

Figure 8:
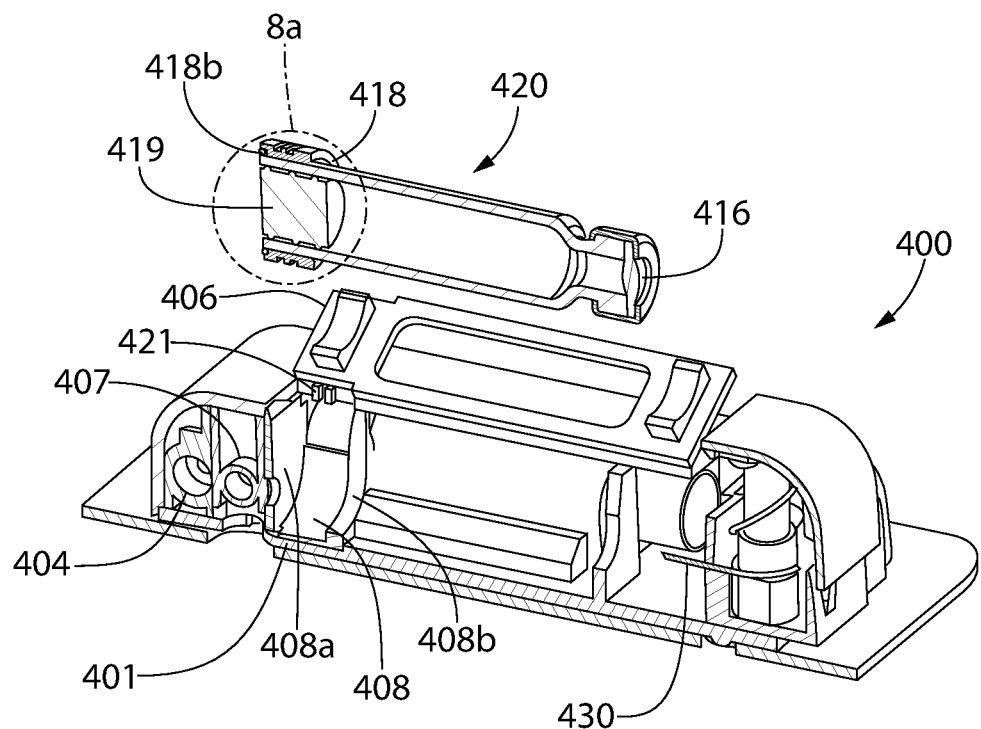
FIG. 8 is a cross sectional trimetric view of the fluid delivery device and the cartridge of FIG. 4.
Figure 8A:
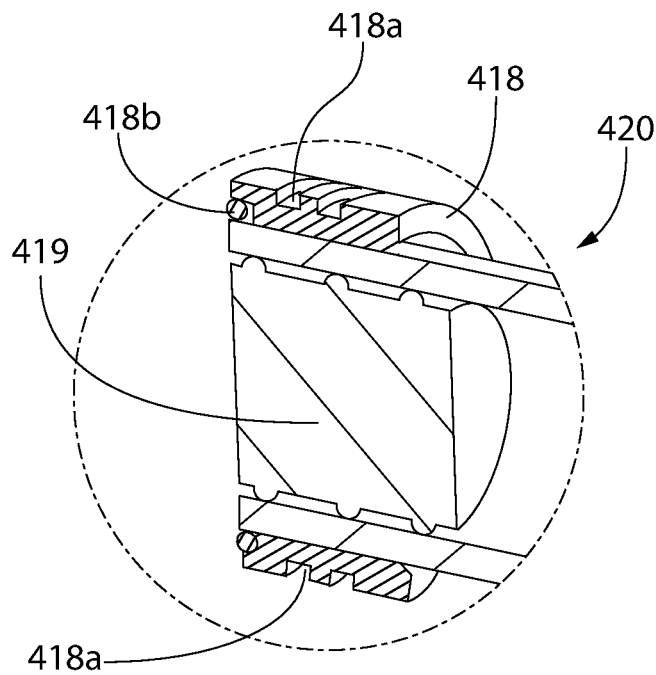
FIG. 8A is an enlarged cross sectional view of the piston end of the cartridge shown in FIG. 8.

Referring to FIG. 8A, in one embodiment, the keyed feature 418 is a separate part that is joined to the cartridge 420 with sufficient strength to resist the maximum force applied to the reservoir by the hydraulic system. In one embodiment the keyed feature 418 is secured to the cartridge 420 using an adhesive. In one embodiment, the keyed feature 418 is secured to the cartridge 420 by a press fit. In one embodiment, the keyed feature 418 is secured to the cartridge 420 by a swage of two pieces where an outer annular piece compresses an inner annular part around the reservoir when they the inner piece is pressed axially into the outer annular piece. In one embodiment, the keyed feature 418 is secured to the cartridge 420 by welding. In one embodiment, the keyed feature 418 is secured to a preparatory surface on the cartridge 420 such as a thin film, an etched surface or an adherent label. In one embodiment, the keyed feature 418 is secured to the cartridge 420 by a sleeve that slips over the end of the cartridge 420 and at least partially over a portion of the seal 418*b*. In one embodiment, the keyed feature 418 is integrally formed into the cartridge 420.

Figure 5:
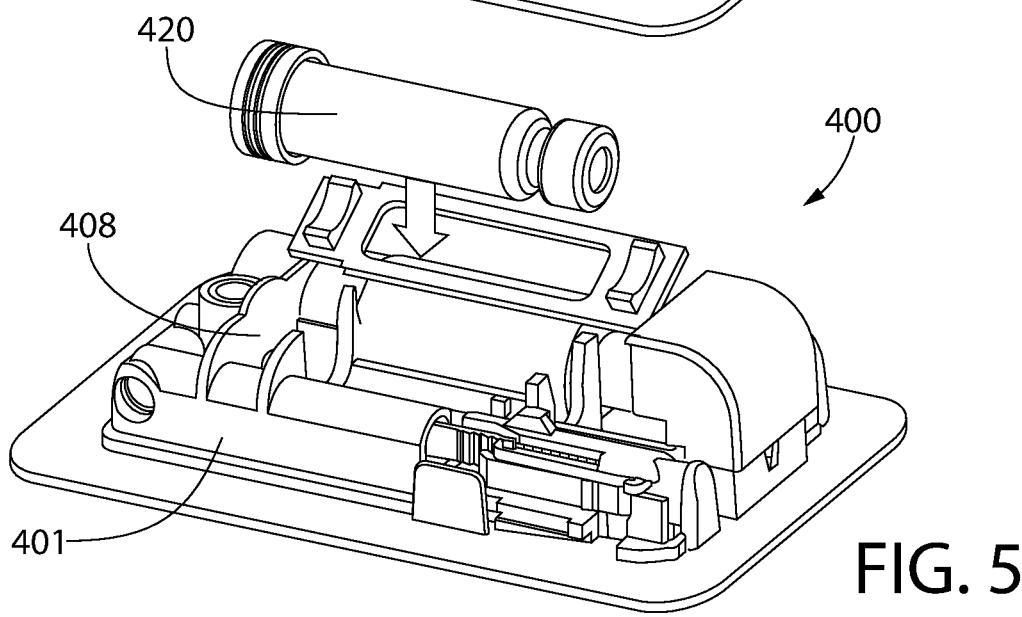
FIG. 5 is a trimetric view of the fluid delivery device and the cartridge of FIG. 4 shown with the housing removed.
Figure 6:
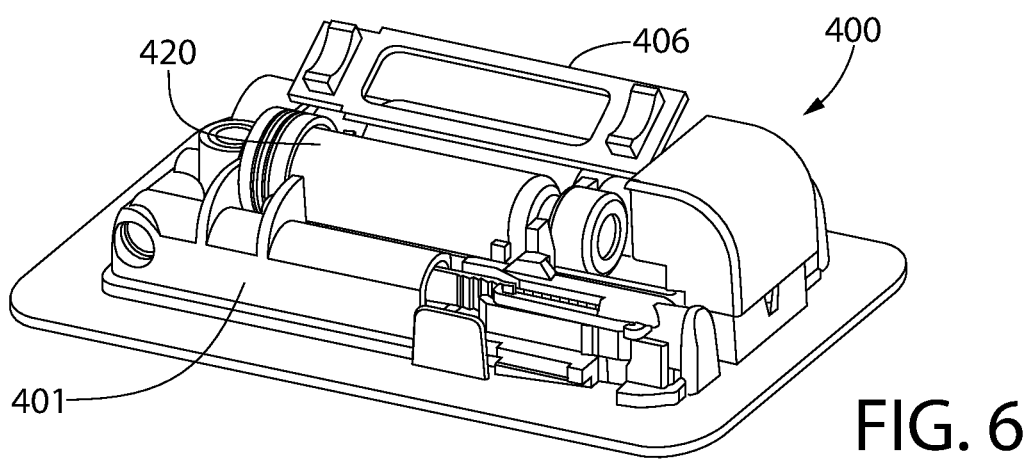
FIG. 6 is a trimetric view of the fluid delivery device and the cartridge of FIG. 4 shown with the cartridge inserted.
Figure 7:
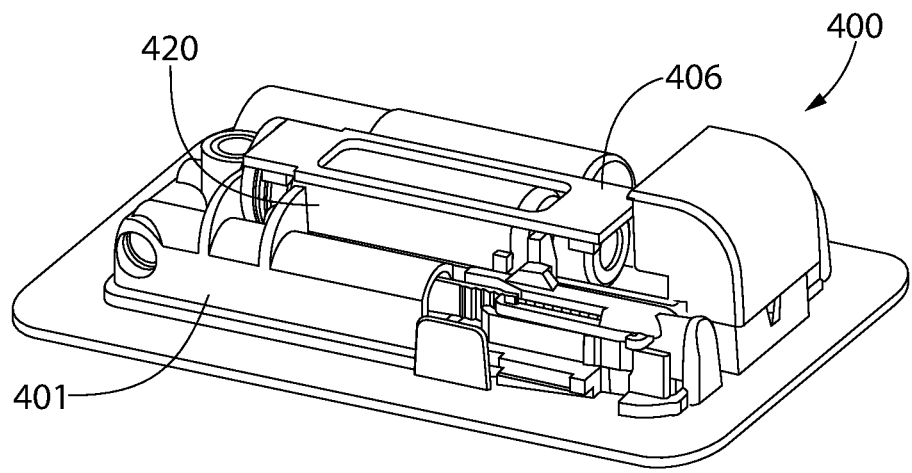
FIG. 7 is a trimetric view of the fluid delivery device and the cartridge of FIG. 4 shown with the cartridge inserted and the housing door closed.

FIG. 5 shows the fluid delivery device 400 with the housing removed to expose the seal receptacle space 408. FIG. 6 show the cartridge 420 inserted into the available space within the hydraulic drive unit 401. In one embodiment, a door 406 is coupled to the housing 402 and configured to be closed over the cartridge 420 to retain the cartridge 420 in the drive unit 401 once the cartridge 420 is in place. The door 406 may be configured to force the cartridge 420 into its fully seated position when the user closes the door 406 as shown in FIG. 7. In one embodiment, there is an interlock that prevents the door 406 from closing without a cartridge 420 being at least partially inserted.

Figure 9:
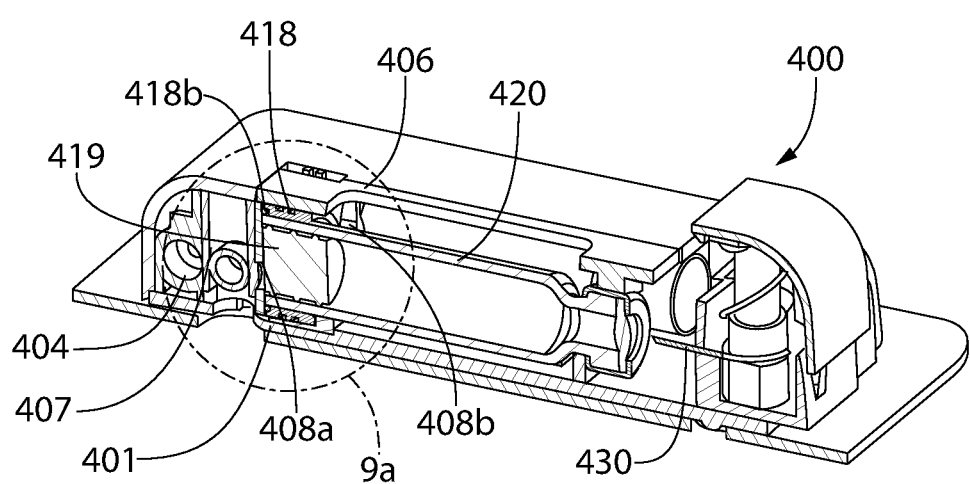
FIG. 9 is a cross sectional trimetric view of the fluid delivery device and the cartridge of FIG. 7.
Figure 9A:
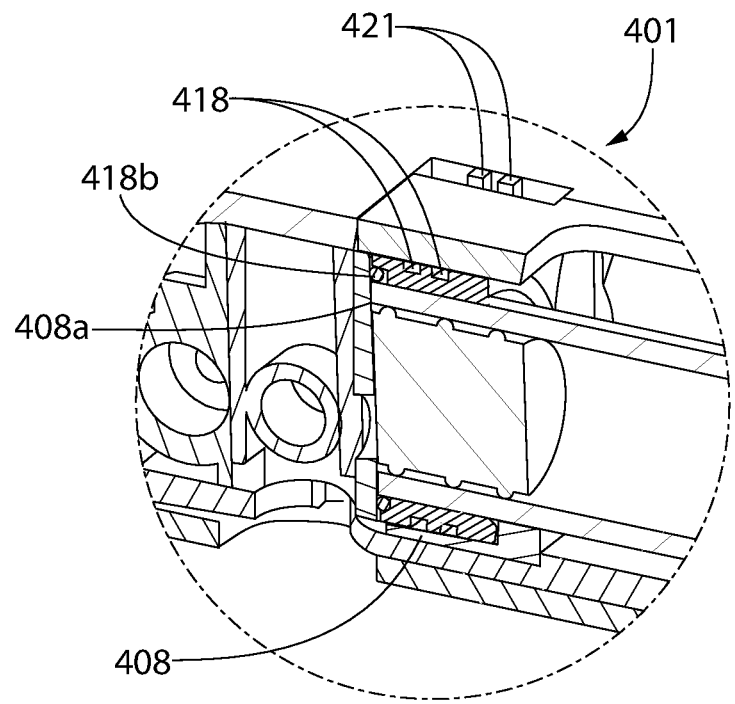
FIG. 9A is an enlarged cross sectional view of the piston end of the cartridge in the fluid delivery device shown in FIG. 9.

FIGS. 9 and 9A show a cross section of one embodiment in which the substantially keyed feature 418 is pressed into the seal receptacle space 408 on insertion of the cartridge 420. In this embodiment, there is a compliant portion or seal 418*b* that slides along the rear surface 408*a* of the seal receptacle space 408. There are shoulders 408*b* on the opposite end of the seal receptacle space 408 that fit with the corresponding end of the keyed feature 418 to force the keyed feature 418 and thus the seal 418*b* against the rear surface 408*a* effecting a seal between the rear surface 408*a* and the piston end of the cartridge 420. In one embodiment, the rear surface 408*a* and the front surface shoulders 408*b* of the seal receptacle space 408 are spaced a distance approximately equal to the distance between the front and rear of the keyed feature 418. In one embodiment, the rear surface 408*a* and the front surface shoulders 408*b* of the seal receptacle space 408 are spaced a distance less than the distance between the front and rear of the keyed feature 418 such that the seal 418*b* is compressed against the rear surface 408*a* once the cartridge is inserted in the drive unit.

In one embodiment, the features 421 are spaced from the rear surface 408*a* a distance approximately equal to the distance the features 418*a* are spaced from the end of the seal 418*b*. In one embodiment, the features 421 are spaced from the rear surface 408*a* a distance less than the distance the features 418*a* are spaced from the end of the seal 418*b* such that the seal 418*b* is compressed against the rear surface 408*a* once the cartridge is inserted in the drive unit. By creating the seal force through the fit of the keyed features 418, 421 the length of the cartridge 420 is not relevant to the creation of the hydraulic fluid seal. In one embodiment, the seal 418*b* is continuous with the keyed feature 418 and the compliance is a result of a thin feature on the end of the keyed feature 418. In one embodiment, the seal 418*b* is an o-ring. In one embodiment, the seal 418*b* is a second shot of compliant material that is co-molded or over-molded with the keyed feature 418. In one embodiment, the seal 418*b* is a second part that is placed in a feature of the keyed feature 418. In one embodiment, the seal 418*b* is integral with the rear surface 408*a* of the seal receptacle space. In one embodiment, there is no compliant material and the fit and surface quality of the keyed feature 418 and the surface 408*a* of the seal receptacle space 408 are sufficient to affect a seal for the hydraulic fluid.

In one embodiment, the keyed feature 418 is comprised of a material that is less compliant than the seal 418*b*. In one embodiment, the keyed feature 418 is comprised of polycarbonate. In other embodiments, the keyed feature 418 is comprised of plastics such as acrylonitrile butadiene styrene (ABS), polypropelene, polysulphone, polyether ether ketone (PEEK), nylon, polyethylene, acrylic, PVC and polystyrene. In one embodiment, the seal 418*b* is comprised of a thermoplastic elastomer (TPE) such as Pebax® with a durometer of less than Shore A 70. In other embodiments, the seal 418*b* is comprised of rubbers including butyl, nitrile and silicone.

Figure 10:
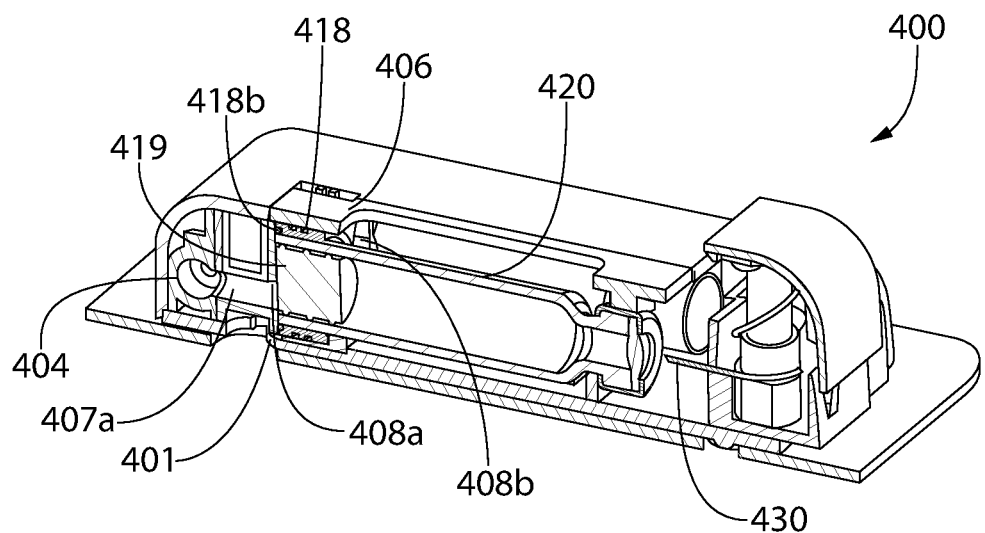
FIG. 10 is a cross sectional trimetric view of the fluid delivery device and the cartridge of FIG. 7 shown with the hydraulic fluid path opened.

In one embodiment, as shown in FIG. 9, the hydraulic fluid is not yet in contact with the rear end of the piston 419. The fluid is still contained within the hydraulic fluid manifold 404 by the hydraulic fluid valve 407. In one embodiment, to bring pressurized hydraulic fluid in contact with the rear of the piston 419 the hydraulic valve 407 is opened by aligning the fluid path through the valve stem 407*a* with the fluid path to the cartridge seal receptacle seal as shown in FIG. 10.

Figure 11:
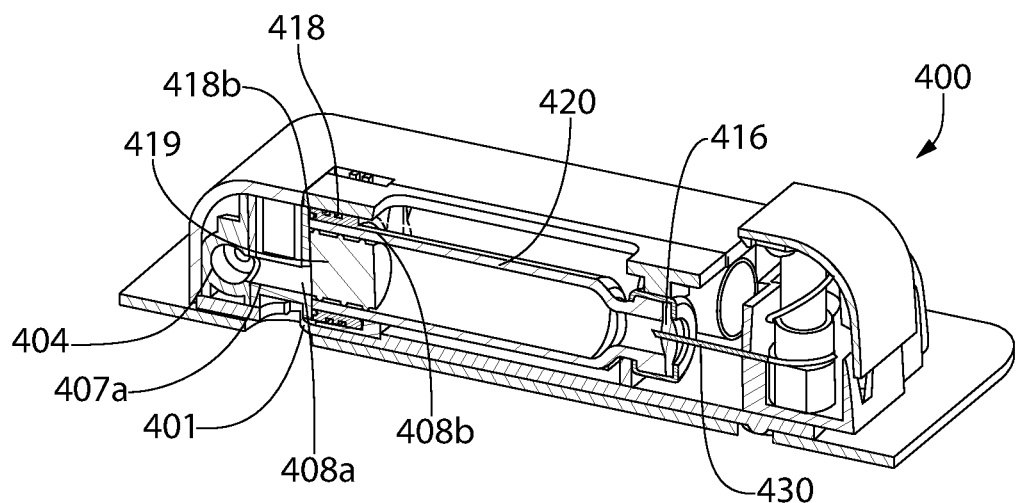
FIG. 11 is a cross sectional trimetric view of the fluid delivery device and the cartridge of FIG. 7 shown with the hydraulic fluid path opened and the septum pierced by the delivery needle.

In one embodiment, to connect the medicament delivery path to the patient, the supply end of the needle 430 is pressed through the piercable element 416 as shown in FIG. 11 making the fluidic connection between the inside of the cartridge 420 and the delivery needle 430.

Figure 12:
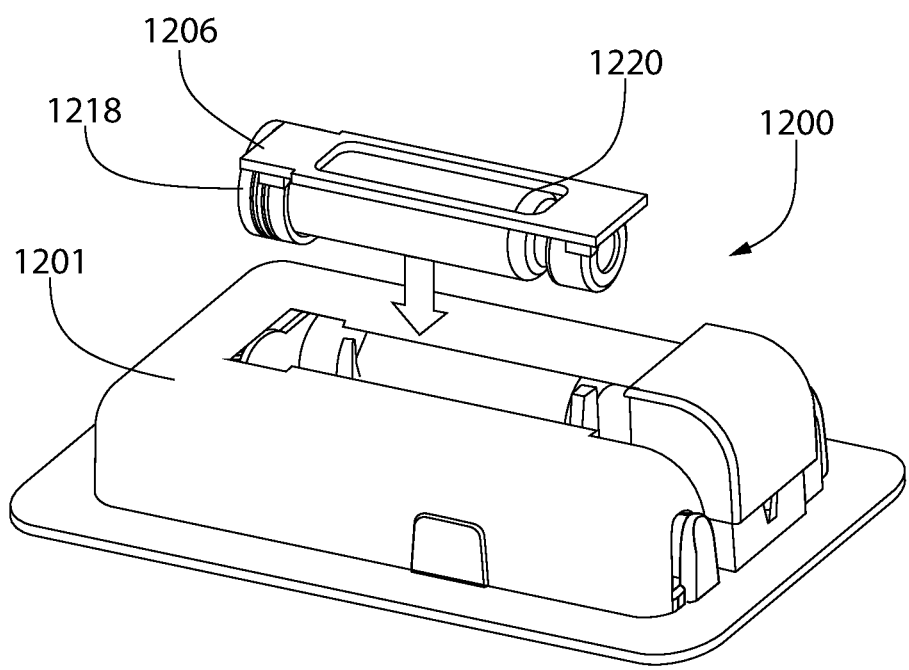
FIG. 12 is a trimetric view of a fluid delivery device with an insertable cartridge in accordance with an exemplary embodiment of the present invention having a cover door connected to the cartridge.

Referring to FIG. 12, a second exemplary embodiment of the fluid delivery device 1200 is shown. In one embodiment, the door 1206 is secured to the keyed feature 1218 and is part of the cartridge assembly 1220. In one embodiment, the door 1206 and the keyed feature 1218 are integrally connected. In one embodiment, the door 1206 and the keyed feature 1218 are two parts but coupled together prior to insertion into the hydraulic drive unit 1201.

In an alternative embodiment, the needle 430 and the needle support system are secured to the door 1206 and the door to the keyed feature 1218 prior to insertion into the hydraulic drive unit 1201.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the methods of the present invention do not rely on the particular order of steps set forth herein, the particular order of the steps should not be construed as a limitation on the claims. Any claims directed to the methods of the present invention should not be limited to the performance of their steps in the order written, and one skilled in the art can readily appreciate that the steps may be varied and still remain within the spirit and scope of the present invention.

I claim:

1. A fluid delivery device comprising:
   a drive unit including a housing, an actuator, and one or more first features; and
   a cartridge comprising a longitudinal axis, wherein the cartridge is filled with a fluid prior to being inserted into the housing, the cartridge having a fluid reservoir sealed at one, first end by a piston and sealed at another, second end by a pierceable septum, the cartridge including or having secured thereto, one or more second features that project radially inwardly or outwardly relative to the longitudinal axis of the cartridge, extend around a circumference of the cartridge, the piston being moveable relative to the cartridge by the actuator once the cartridge is inserted into the drive unit,
   wherein, when the cartridge is positioned within the housing the one or more first features of the drive unit are mated with the one or more second features of the cartridge such that the cartridge is translatable relative to the drive unit in a direction perpendicular to the longitudinal axis and prevented from translating relative to the drive unit in a direction parallel to the longitudinal axis.

2. The fluid delivery device of claim 1, wherein the actuator is a hydraulically driven actuator and the cartridge is sealed to the drive unit by a seal.

3. The fluid delivery device of claim 2, wherein the seal is secured to the fluid reservoir by a sleeve that slips over the cartridge and at least partially over a portion of the seal.

4. The fluid delivery device of claim 3, wherein the sleeve includes the one or more second features.

5. The fluid delivery device of claim 2, wherein the seal is coupled to the one or more second features.

6. The fluid delivery device of claim 2, wherein the seal is a ring secured to an exterior of the cartridge.

7. The fluid delivery device of claim 2, wherein the seal is an integral feature of the cartridge.

8. The fluid delivery device of claim 2, wherein the seal includes at least two pieces that are coupled together from opposing lateral sides of the cartridge and create a friction fit with the cartridge.

9. The fluid delivery device of claim 2, wherein the seal includes a first flexible portion proximate an end of the cartridge and a second flexible portion, the second flexible portion being less flexible than the first flexible portion and including the one or more second features.

10. The fluid delivery device of claim 2, wherein at least one of the one or more first features and/or at least one of the one or more second features includes a tapered lead-in configured to help guide the cartridge into place during insertion and compress the seal against the cartridge.

11. The fluid delivery device of claim 2, wherein the seal is provided on the end of the cartridge and mating the one or more second features with the one or more first features compresses the seal against the drive unit to seal the cartridge to the drive unit.

12. The fluid delivery device of claim 1, wherein the one or more first features are generally rectangular projections and the one or more second features are grooves configured to intermesh with the generally rectangular projections.

13. The fluid delivery device of claim 1, wherein the one or more first features are grooves and the one or more second features are generally rectangular projections configured to intermesh with the grooves.

14. The fluid delivery device of claim 1, wherein the fluid delivery device includes a door coupled to the housing the door being rotatable relative to the housing to cover the cartridge and seat the cartridge into position within the drive unit.

15. The fluid delivery device of claim 1, wherein the cartridge includes a cover structure configured to be generally flush with the housing of the drive unit when the cartridge is fully inserted into the drive unit.

16. The fluid delivery device of claim 1 further comprising:
   a needle assembly having a needle, the needle having a delivery end and a fluid coupling end, the fluid coupling end being fluidly disengaged from the fluid reservoir in an initial position, the delivery end extending past a bottom surface of the housing of the drive unit in a deployed position and the fluid coupling end extending through the pierceable septum and fluidly coupled with the fluid reservoir in the deployed position.

17. A cartridge for insertion in a fluid delivery device, the cartridge comprising:
   a longitudinal axis;
   a reservoir filled with a fluid, the reservoir sealed at one, first end by a movable piston and sealed at another, second end by a pierceable septum; and
   one or more radial projecting and circumferentially extending keyed features configured to align and mate with one or more corresponding keyed features of the fluid delivery device allowing the cartridge to be inserted into the fluid delivery device and, while mated with the one or more corresponding keyed features of the fluid delivery device, prevent translation of the cartridge in a direction along the longitudinal axis and permit translation of the cartridge in a direction perpendicular to the longitudinal axis, wherein the cartridge is configured to be inserted into the fluid delivery device about a direction which is perpendicular to the longitudinal axis of the cartridge.

18. A fluid delivery device comprising:
a drive unit including a housing, an actuator, and one or more first features; and
a cartridge comprising a longitudinal axis, wherein the cartridge is filled with a fluid prior to being inserted into the housing about a direction which is perpendicular to the longitudinal axis of the cartridge, the cartridge having a fluid reservoir sealed at one end by a movable piston and sealed at another end by a pierceable septum, the piston being moveable by the actuator once the cartridge is inserted into the drive unit,
wherein the fluid delivery device includes a door coupled to the housing, the door being rotatable relative to the housing to cover the cartridge and seat the cartridge into position within the drive unit, and
wherein, when the cartridge is positioned within the housing the one or more first features of the drive unit are mated with one or more second features of the cartridge such that the cartridge is translatable relative to the drive unit in a direction perpendicular to the longitudinal axis and prevented from translating relative to the drive unit in a direction parallel to the longitudinal axis.

19. A fluid delivery device comprising:
a drive unit including a housing, an actuator, and one or more first features; and
a cartridge comprising a longitudinal axis, wherein the cartridge is filled with a fluid prior to being inserted into the housing about a direction which is perpendicular to the longitudinal axis of the cartridge, the cartridge having a fluid reservoir sealed at one end by a movable piston and sealed at another end by a pierceable septum, the piston being moveable by the actuator once the cartridge is inserted into the drive unit,
wherein the cartridge includes a cover structure configured to be generally flush with the housing when the cartridge is fully inserted into the drive unit, and
wherein, when the cartridge is positioned within the housing the one or more first features of the drive unit are mated with one or more second features of the cartridge such that the cartridge is translatable relative to the drive unit in a direction perpendicular to the longitudinal axis and prevented from translating relative to the drive unit in a direction parallel to the longitudinal axis.

20. The fluid delivery device of claim 19 further comprising:
an adhesive bottom surface configured to be coupled to a skin surface when the fluid delivery device is in use.

21. The fluid delivery device of claim 20, wherein the direction is perpendicular to the adhesive bottom surface.

22. The fluid delivery device of claim 21, wherein the cartridge is configured to pass through an opening in the housing which is located on a first side of the housing, wherein the adhesive bottom surface is located on a second side of the housing which is opposite the first side of the housing.

23. The fluid delivery device of claim 20, wherein the cartridge is configured to pass through an opening in the housing which is located on a first side of the housing, wherein the adhesive bottom surface is located on a second side of the housing which is opposite the first side of the housing.

24. The fluid delivery device of claim 1 further comprising:
an adhesive bottom surface configured to be coupled to a skin surface when the fluid delivery device is in use.

25. The fluid delivery device of claim 18 further comprising:
an adhesive bottom surface configured to be coupled to a skin surface when the fluid delivery device is in use.

26. The fluid delivery device of claim 1, wherein the one or more second features extend around the entire circumference of the cartridge.

27. The cartridge of claim 17, wherein the one or more keyed features extend around the entire circumference of the cartridge.

28. The fluid delivery device of claim 1, wherein the one or more second features are located more proximate to the first end of the cartridge than to the second end of the cartridge which comprises the pierceable septum.

29. The cartridge of claim 17, wherein the keyed features are located more proximate to the first end of the cartridge than to the second end of the cartridge which comprises the pierceable septum.

* * * * *